(12) United States Patent
McNair

(10) Patent No.: US 10,410,750 B1
(45) Date of Patent: Sep. 10, 2019

(54) PREDICTING RESPIRATORY DISTRESS

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 15/855,043

(22) Filed: Dec. 27, 2017

Related U.S. Application Data

(62) Division of application No. 14/687,652, filed on Apr. 15, 2015.

(60) Provisional application No. 61/979,855, filed on Apr. 15, 2014.

(51) Int. Cl.
*G16H 50/20* (2018.01)

(52) U.S. Cl.
CPC .................................. *G16H 50/20* (2018.01)

(58) Field of Classification Search
CPC ...................................................... G16H 50/20
USPC ............................................................ 702/19
See application file for complete search history.

(56) References Cited

PUBLICATIONS

Douglas T. Hicks, "Activity-Based Costing . . . Making It Work for Small and Mid-Sized Companies," Second Edition, 1999, 357 pages (hard cover book mailed by Fed Ex Feb. 28, 2017).
Gravenstein, et al., "Capnography," Second Edition, 2011, 474 pages (hard cover book mailed by Fed Ex Feb. 28, 2017).
Preinterview First Office Action dated Mar. 22, 2018 in U.S. Appl. No. 14/687,652, 3 pages.

*Primary Examiner* — Jerry Lin
(74) *Attorney, Agent, or Firm* — Shook, Hardy & Bacon L.L.P.

(57) ABSTRACT

A system, methods, and computer-readable media are provided for the automatic identification of patients having an elevated near-term risk of pulmonary function deterioration or respiratory distress. Embodiments of the invention are directed to event prediction, risk stratification, and optimization of the assessment, communication, and decision-making to prevent respiratory events in humans, and in one embodiment take the form of a platform for wearable, mobile, untethered monitoring devices with embedded decision support. Respiratory information is obtained over one or a plurality of previous time intervals, to classify a likelihood of events leading to an acute respiratory decompensation event within a future time interval. In an embodiment, the risk prediction is based a plurality of nonlinearity measures of capnometry information over the previous time interval(s), and the risk for an acute respiratory decompensation event determined using an ensemble model predictor on the nonlinearity measures.

14 Claims, 13 Drawing Sheets

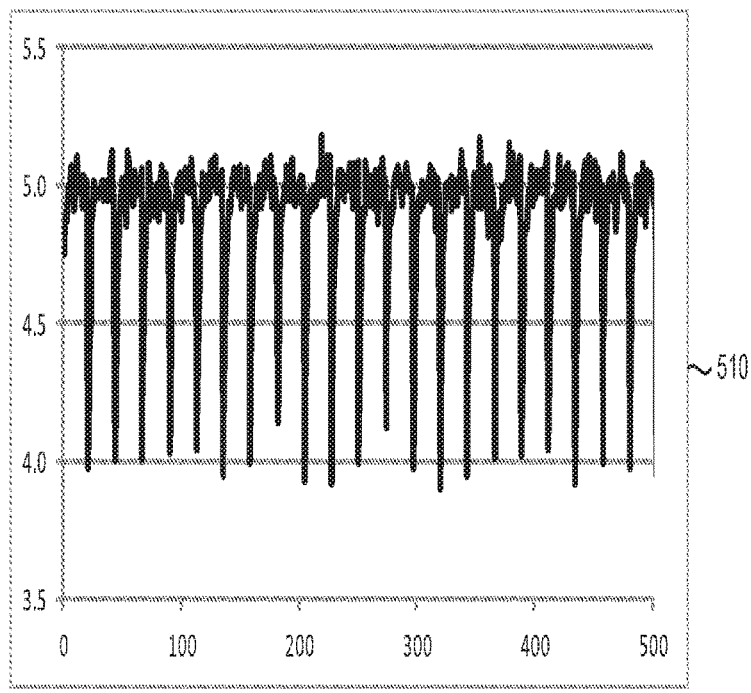
FIG. 5A.
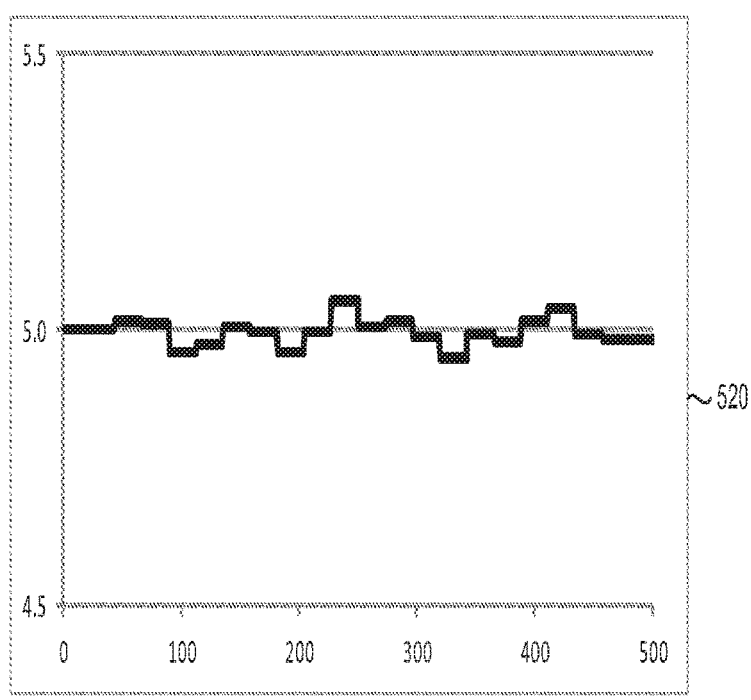

|       | 552   |       | 554   |          |       | 556   |
|-------|-------|-------|-------|----------|-------|-------|
| raw_t | t_et  | etco2 | co2   | sharkfin | noise | graph |
| 1     |       |       | 4.76  | 4.81     | -0.12 | 5.00  |
| 2     |       |       | 4.88  | 4.89     | -0.01 | 5.00  |
| 3     |       |       | 4.87  | 4.94     | -0.15 | 5.00  |
| 4     |       |       | 4.98  | 4.96     | 0.05  | 5.00  |
| 5     |       |       | 4.97  | 4.98     | -0.01 | 5.00  |
| 6     |       |       | 4.96  | 4.99     | -0.07 | 5.00  |
| 7     |       |       | 5.06  | 4.99     | 0.16  | 5.00  |
| 8     |       |       | 5.00  | 5.00     | 0.00  | 5.00  |
| 9     |       |       | 4.91  | 5.00     | -0.21 | 5.00  |
| 10    |       |       | 4.97  | 5.00     | -0.07 | 5.00  |
| 11    |       |       | 5.02  | 5.00     | 0.04  | 5.00  |
| 12    |       |       | 5.10  | 5.00     | 0.24  | 5.00  |
| 13    |       |       | 4.98  | 5.00     | -0.05 | 5.00  |
| 14    |       |       | 5.02  | 5.00     | 0.05  | 5.00  |
| 15    |       |       | 5.03  | 5.00     | 0.07  | 5.00  |
| 16    |       |       | 4.92  | 5.00     | -0.19 | 5.00  |
| 17    |       |       | 5.03  | 5.00     | 0.06  | 5.00  |
| 18    |       |       | 4.97  | 5.00     | -0.07 | 5.00  |
| 19    |       |       | 5.00  | 5.00     | 0.01  | 5.00  |
| 20    |       |       | 5.01  | 5.00     | 0.02  | 5.00  |
| 21    | 21    | 5.00  | 3.98  | 4.00     | -0.05 | 5.00  |
| 22    |       |       | 4.39  | 4.42     | -0.08 | 5.00  |
| 23    |       |       | 4.52  | 4.67     | -0.35 | 5.00  |
| 24    |       |       | 4.85  | 4.81     | 0.09  | 5.00  |
| 25    |       |       | 4.90  | 4.89     | 0.03  | 5.00  |
| 26    |       |       | 5.00  | 4.94     | 0.16  | 5.00  |
| 27    |       |       | 4.95  | 4.96     | -0.03 | 5.00  |
| 28    |       |       | 4.96  | 4.98     | -0.05 | 5.00  |
| 29    |       |       | 4.96  | 4.99     | -0.07 | 5.00  |
| 30    |       |       | 4.98  | 4.99     | -0.04 | 5.00  |
| 31    |       |       | 4.97  | 5.00     | -0.06 | 5.00  |
| 32    |       |       | 4.99  | 5.00     | -0.02 | 5.00  |
| 33    |       |       | 5.00  | 5.00     | 0.01  | 5.00  |
| 34    |       |       | 4.95  | 5.00     | -0.11 | 5.00  |
| 35    |       |       | 5.00  | 5.00     | 0.01  | 5.00  |
| 36    |       |       | 4.99  | 5.00     | -0.02 | 5.00  |
| 37    |       |       | 4.97  | 5.00     | -0.07 | 5.00  |
| 38    |       |       | 4.95  | 5.00     | -0.12 | 5.00  |
| 39    |       |       | 5.00  | 5.00     | -0.01 | 5.00  |
| 40    |       |       | 5.08  | 5.00     | 0.19  | 5.00  |
| 41    |       |       | 5.12  | 5.00     | 0.29  | 5.00  |
| 42    |       |       | 4.91  | 5.00     | -0.22 | 5.00  |
| 43    |       |       | 4.96  | 5.00     | -0.10 | 5.00  |
| 44    | 44    | 5.02  | 4.01  | 4.00     | 0.02  | 5.02  |

(DATA CONTINUES)

680

```
library(pROC)

ds4 <- read.csv(file="C:/0_cerdsm/IP/capnometry/roc.csv")
roc1 <- roc(ds4[,1] ~ ds4[,2], percent=TRUE,
# arguments for auc
  partial.auc=c(100, 90), partial.auc.correct=TRUE,
  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)

# column-major
dsm <- matrix(c(4,1,0,11), ncol=2)
fisher.test(dsm)
```

*FIG. 6B.*

```
library(waveslim)
library(nonlinearTseries)
library(nlts)

# spectral density by wavelet-based Maximum Likelihood Estimation (MLE) for a Fractional Difference Process
(FDP)
fdp.sdf <- function(freq, d, sigma2=1){
  sigma2/((2*sin(pi*freq))^2)^d
} decibels transform for power spectrum
dB <- function(x) 10 * log10(x)

# radix-2 periodogram
per <- function(z) {
  n <- length(z)
  (Mod(fft(z))**2/(2*pi*n))[1:(n %/% 2 + 1)]
} import demeaned data as data.frame
ds3 <- read.csv(file="C:/0_cerdsm/IP/capnometry/dsm_d02.csv")

# coerce to vector, convert to time series object
mts <- ts(unlist(ds3$g), frequency=1)

# normalize
mts.max <- max(mts)
mts.min <- min(mts)
mts.p <- (mts - mts.min)/(mts.max - mts.min)

# export data as data.frame
ds4 <- data.frame(ds3$t,mts.p)
write.csv(ds4,file="C:/0_cerdsm/IP/capnometry/d02dtpwn.csv", row.names=FALSE)

.
                               .
                               .
```

CONTINUES IN FIG. 7B

*FIG. 7A.*

CONTINUES FROM FIG. 7A

.
.
.

700

```
# eval nonlinearity of time series
nl.LR <- rep(NA,50)
nl.Keen <- rep(NA,50)
nl.Wht <- rep(NA,50)
nl.Teras <- rep(NA,50)
nl.McLeod <- rep(NA,50)
nl.LM <- rep(NA,50)
nl.Tukey <- rep(NA,50)
nl.Ljung <- rep(NA,50)
for (i in 1:50){
   start <- 200*(i - 1) + 1
   end <- start + 199
   nl.test <- nonlinearityTest(mts.p[start:end], verbose=FALSE)
   nl.LR[i] <- nl.test$TarTest$p.value
   nl.Keen[i] <- nl.test$Keenan$p.value
   nl.Wht[i] <- nl.test$White$p.value
   nl.Teras[i] <- nl.test$Terasvirta$p.value
   nl.McLeod[i] <- max(nl.test$McLeodLi$p.values)
   nl.LM[i] <- add.test(mts.p[start:end], order=3)[3]
   nl.Tukey[i] <- lin.test(mts.p[start:end], order=3)[5]
   nl.Ljung[i] <- portman.Q(mts.p[start:end], K=3)[5]
}
median(nl.LR[])
median(nl.Keen[])
median(nl.Wht[])
median(nl.Teras[])
median(nl.McLeod[])
median(nl.LM[])
median(nl.Tukey[])
median(nl.Ljung[])
```

.
.
.

CONTINUES IN FIG. 7C

*FIG. 7B.*

CONTINUES FROM FIG. 7B

.
.
.

```
# calc third-order time-reversibility statistic, iff < 0 then nonlinear; iff min < -1.0e-03 then signif nonlin
# since linear stochastic series are symmetric under time reversal, this statistic may be used for
# testing the assertion that the data was generated from a stationary linear stochastic process or not.
ts <- rep(NA,10000)
for (i in 1:10000){
  ts[i] <- timeReversibility(ds4[,2], tau=i)
}
min(ts[])

# calc detrended fluctuation analysis estimate of Hurst exponent
dfa.analysis <- dfa(time.series=ds4[,2], npoints=10, window.size.range=c(10,1000), do.plot=TRUE)
cat("Normal range: 0.341 to 0.413 -- Estimated: ", round(estimate(dfa.analysis),3),"\n")

# construct 0-to-10 Hz MLE periodogram from first 8,192 samples
# 50 msec (20 Hz)
freq <- 0:4096/8192
wf <- "d4"
j <- 13
ds4.mle <- fdp.mle(ds4[1:8192,2], wf, j)
ds4.per <- 2*pi*per(ds4[1:8192,2])
par(mfrow=c(1,1), las=0, pty="m")
plot(freq, dB(ds4.per), type="l", xlab="Frequency", ylab="Spectrum")
lines(freq, dB(fdp.sdf(freq, ds4.mle$parameters[1], ds4.mle$parameters[2]/2)), col=2)

# show timeseries length
length(ds3$g)
```

*FIG. 7C.*

PREDICTING RESPIRATORY DISTRESS

CROSS-REFERENCE TO RELATED APPLICATIONS

This application is a divisional of U.S. application Ser. No. 14/687,652, titled "PREDICTING RESPIRATORY DISTRESS," filed Apr. 15, 2015, which claims the benefit of U.S. Provisional Application No. 61/979,855, titled "PREDICTING RESPIRATORY DISTRESS," filed on Apr. 15, 2014, both of which are hereby expressly incorporated by reference in their entirety.

INTRODUCTION

Asthma and chronic obstructive pulmonary diseases, such as COPD, bronchitis, bronchiectasis, emphysema, and the like, are long-term conditions that affect the airways. Chronic lower respiratory disease, primarily COPD and asthma, was the third leading cause of mortality in the U.S. in 2011, and 15 million Americans report that they have been diagnosed with COPD. Classic symptoms include dyspnea, tightness in the chest, wheezing, and coughing. The objective of management is for people to be symptom-free and able to lead an active life. This is achieved by treatment, preferably personalized to the particular needs and circumstances of each individual patient, and by educating each patient as to the exposures or events that trigger acute the respiratory exacerbations they experience, so as to enable the patient to avoid these triggers as much as possible.

The causes of obstructive lung diseases are diverse, including genetic and environmental causes, and cure is not generally possible, although resolution can sometimes be achieved in occupational asthma. Occupational factors account for about 10% of cases of newly incident asthma in adults of working age. The goals of care in chronic obstructive lung diseases are to control the condition, so as to reduce disease progression; to reduce the severity of disease and the morbidity that is associated with concomitant conditions; and to minimize episodes of acute decompensation and respiratory distress or respiratory failure.

For persons with asthma or COPD, acute, unplanned respiratory function deterioration resulting in the need for emergency department or in-patient hospital care is a frequent problem worldwide. In the U.S. in 2011, AHRQ records indicate that 1.1 million in-patient admissions, 2.9 million emergency department (ED) episodes, and 8.9 million doctor office visits occurred for individuals with a principal diagnosis in the ICD-9 code 491.0-494.9 range, resulting in $26 billion of annual in-patient charges, $4.3 billion ED charges, and more than $56 billion in annual direct-care health expenses overall. The weighted average mortality rate was 0.95% for in-patients admitted to hospital with principal diagnosis in this range of ICD-9 codes during 2011. The likelihood of acute pulmonary insufficiency increases substantially with advancing age and comorbid health conditions. The average medical charges associated with an in-patient episode resulting from an acute exacerbation of a principal condition in the ICD-9 code 491.0-494.9 range presently exceed $26,000, and the total acute-care cost of acute respiratory events in the context of chronic obstructive lung disease is expected to reach $28 billion in 2020.

Critical asthma syndrome comprises life-threatening asthma and status asthmaticus. Life-threatening asthma exacerbations are defined as dyspnea so severe that the patient is unable to speak, markedly decreased peak expiratory flow (PEF)<25% of a patient's personal best, and failure to respond to bronchodilator medication and intravenous corticosteroids. Critical asthma syndrome cases require emergency care, and most cases require hospitalization, usually in an intensive care unit. Among asthmatics, those with the critical asthma syndrome are the most difficult to manage.

Procedural prevention programs attempting to reduce the incidence of acute respiratory distress in the setting of COPD or asthma have to-date had mixed effectiveness, in part because the preventive measures address only a subset of the antecedent factors that lead to these events and in part because they place a portion of the burden of event-prevention upon personnel other than the person who is at risk.

SUMMARY

Systems, methods and computer-readable media are provided for the automatic identification of patients having an elevated near-term risk of pulmonary function deterioration or respiratory distress. Embodiments of the invention are directed to event prediction, risk stratification, and optimization of the assessment, communication, and decision-making to prevent respiratory events in humans, and in one embodiment take the form of a platform for wearable, mobile, untethered monitoring devices with embedded decision support. Thus, the aim of embodiments of the present invention relates to automatically identifying persons who are at risk for acute respiratory deterioration through the use of an inexpensive, noninvasive, portable electronic device and sensors equipped with signal-processing software and statistical predictive algorithms that calculate nonlinearity properties of capnometry timeseries acquired by the device. The measurements and predictive algorithms provide for use in general acute-care and chronic-care venues and afford a degree of robustness against variations in individual anatomy and sensor placement. In some embodiments, the present invention provides a leading indicator of near-term future abnormalities, proactively notifying clinicians caring for the user and providing the care providers with sufficient advance notice (such as hours, days, or weeks in advance) to enable effective preventive maneuvers to be undertaken. In one exemplary embodiment, the device is integrated with case-management software and electronic health record decision-support systems, including occupational health, health insurance, and disability assessment decision-support systems.

In one aspect, a method is provided for automatically predicting an acute respiratory decompensation event that is likely to result in the need for acute medical attention. The method includes the step obtaining capnometry signals representative of capnometry of an individual; detecting the presence of abnormal timeseries nonlinearity properties of capnometry measurements in said signals. The method also includes the steps of determining, utilizing an objective function, a capnometry nonlinearity score (CNS) from the signals based on one or a plurality of previous time intervals. In an embodiment, the method also includes and determining a difference between a plurality of metrics comprising the CNS and a reference value to classify the likelihood of events leading to pulmonary function decompensation within a future time interval, wherein a difference from the reference value is indicative of increased risk for acute respiratory distress, wherein the reference value may be determined based on clinical parameters associated with the individual such age, mobility, pulmonary function decompensation, or other clinical parameters associated with the individual. In one embodiment, the method further includes providing a notification when an increased risk for acute respiratory distress is determined. In some embodiments, this notification may be communicated to a health care provider and/or may be communicated to the individual by means of an audible alarm, text message, or phone call or other electronic notification.

BRIEF DESCRIPTION OF THE DRAWINGS

The present invention is described in detail below with reference to the attached drawing figures, wherein:

FIGS. 5A and 5B depicts aspects of expiratory timeseries data and computations, in accordance with embodiments of the invention;

FIG. 6B depicts an example of a computer program for determining the ROC curve provided in FIG. 6A, in accordance with embodiments of the invention; and FIGS. 7A-7C illustratively provide an example embodiment of a computer program routine for determining nonlinearity measures of capnometry-information timeseries and performing an ensemble of measures, in accordance with an embodiment of the invention.

DETAILED DESCRIPTION

Figure 1:
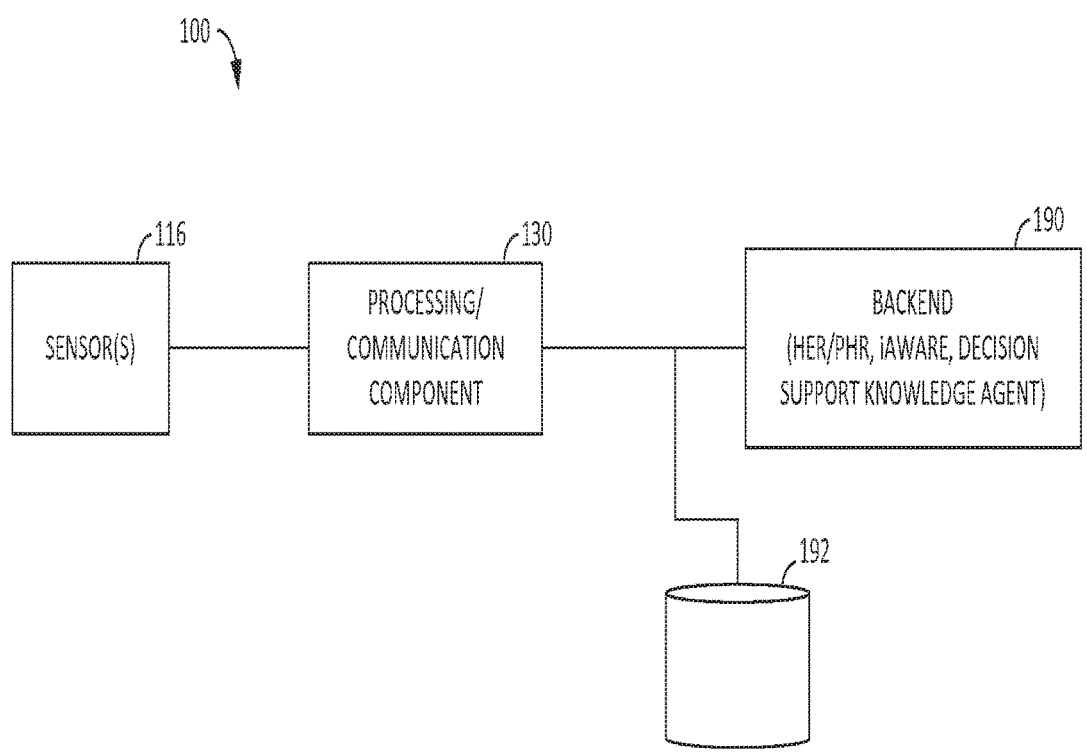
FIG. 1 depicts aspects of an operating environment suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

At a high level, embodiments of the invention pertain to monitoring human patients and quantitatively predicting whether or not an elevated risk of acute deterioration of pulmonary function prevails within an acute time interval of up to several weeks subsequent to computing the prediction and, if such is the case, informing the care provider clinicians' decisions and interventions to mitigate the risk and prevent the occurrence of acute, unplanned emergency department episodes or hospital admissions and concomitant morbidity in such patients.

More specifically, embodiments of the invention provide systems and methods for the automatic identification of patients having an elevated near-term risk of pulmonary function deterioration or respiratory distress. In particular, embodiments of the invention are directed to event prediction, risk stratification, and optimization of the assessment, communication, and decision-making to prevent respiratory events in humans, and in one embodiment take the form of a platform for wearable, mobile, untethered monitoring devices with embedded decision support. Accordingly, embodiments of the invention facilitate automatically identifying persons who are at risk for acute respiratory deterioration through the use of an inexpensive, noninvasive, portable electronic device and sensors equipped with signal-processing software and statistical predictive algorithms that calculate nonlinearity properties of capnometry timeseries acquired by the device.

As described above, existing procedural prevention programs attempting to reduce the incidence of acute respiratory distress in the setting of COPD or asthma have to-date had mixed effectiveness, in part because the preventive measures address only a subset of the antecedent factors that lead to these events and in part because they place a portion of the burden of event-prevention upon personnel other than the person who is at risk. In that connection, one motivation for some embodiments of the invention is that, were people with obstructive lung disease whose near-term risks of acute pulmonary exacerbations are recently elevated or increasing notified of that risk or risk-increase, many such patients would respond to the notifications by proactively self-initiating preventive measures, including temporarily adjusting their daily activities and exposures to respiratory irritants and contacting caregivers for help. Psychologically, this is far preferable to patient passivity and reactive responses by caregivers, insofar as persons at risk of respiratory insults not only fear such events; they also fear loss of independence and freedom.

As further noted above, acute decompensation of respiratory function is associated with common chronic diseases that obstruct the airways, such as asthma and chronic obstructive lung disease (COPD). But it is also associated with less common obstructive conditions such as cystic fibrosis. Acute exacerbation of obstructive respiratory symptoms may also be intercurrent with, or secondary to, Alzheimer's or other forms of dementia where obstruction is due to generalized weakness, inattention to self-care, and poor bronchial toilet; scoliosis or other skeletal conditions that compromise the mechanics of breathing; or Parkinson's disease or ALS or other neurologic conditions accompanied by difficulty clearing bronchial secretions. However, while the absence of such conditions does reduce respiratory risk to a degree, it does not exclude the possibility of acute respiratory distress. It is for this reason that so much effort has been expended over the past 30 years on developing diagnostic tests, such as FEV1/FVC ratio, exhaled nitric oxide measurement, and other metrics.

Mechanisms and types of pulmonary function decompensation have been the subject of several studies. Seasonal allergen and other environmental factors account for a high percentage of respiratory events and subsequent services utilization in community-dwelling older adults as well as children. However, existing oximetric, capnometric, nitric oximetric, spirometric, and other prior art methods, while able to determine the overall severity of respiratory illness, are relatively insensitive and inaccurate with regard to predicting future acute respiratory distress events.

Further, anxiety or other emotional triggers play a significant role in the onset of acute respiratory distress in individuals with asthma or COPD. However, other approaches to diagnostic and monitoring spirometry and nitric oximetry methods typically entail short (1- to 15-second) tests that encompass too small a time interval to have a realistic chance of capturing the influence of fluctuating emotions or time-varying adrenergic and cholinergic neuroendocrine phenomena that can precipitate acute respiratory distress.

Acute exacerbations of asthma and COPD are frequent causes of absenteeism among persons of employment age. In 2008, asthma caused 14.2 million missed days of work. Additionally, respiratory conditions are frequently the subject of occupational medicine and health insurance decision-making. Determination of bona fide disability in an accurate and fair manner has major public health importance and financial significance for employers and insurers. In the 4-year interval between January 2009 and December 2012, 5.9 million people in the U.S. were added to the Social Security Disability program. This contrasts with on 2.5 million jobs that were added during the same 4 years. Approximately 4% (470 thousand) of the 10.9 million people on U.S. federal disability have claims based on chronic respiratory ailments.

Besides accurate assessment of true functional impairments, accurate and reliable ascertainment of malingering and attempts to defraud health plans, employers, and insurers by persons' factitiously simulating respiratory impairment is of great economic importance. Medical malingering for the pursuit of external, financial gain is an increasingly significant social and economic problem in recent years. Persons who wish to be classified as disabled to be placed on the public dole routinely attempt to fabricate a dossier of evidence of health problems. Often, they present themselves at hospital emergency departments in serial weekly or monthly episodes to accomplish this, co-opting health care workers in the construction of the dossier. Acute respiratory ailments are a favorite among malingerers. Compared to malingering involving psychiatric or pain symptoms, covertly injecting saliva to produce sepsis, ingesting rat poison or warfarin to produce a bleeding disorder, ingesting OTC laxatives to cause diarrhea, or feigning seizures or syncope, the pattern of paroxysmal onset and rapid abatement of respiratory signs and symptoms is ideal for perpetrators of medical fraud. In respiratory malingering, the brief play-acting does not involve significant personal injury or health risk. The situation acted-out does not entail that the actor will undergo painful, invasive, inconvenient, time-consuming examinations, unpleasant treatments, or social stigmatization. The short duration of the attack and the fact that prior art pulmonary function tests can be deliberately manipulated by the malingerer mean that there is low risk of fraud detection. In short, the intermittent, paroxysmal, and emergent features of obstructive respiratory illness are especially congenial for fraud.

Once medical intervention in the ambulance or emergency department commences, the fraudster undertakes to abate his/her simulated breathing abnormalities. The emergency care providers are satisfied and relieved that their treatment has yielded the desired effect, they author documentation of that effect and deposit it in the patient's health record, and the deception is complete. Among emergency medicine personnel in the U.S., the act of repeatedly mimicking physical signs of moderate to severe acute illness over a period of months to years with the aim of fraudulently obtaining public disability payments is termed "pulling a Jenny-Sue." Such deception costs society billions each year. Emergency medicine staff are understandably reluctant to assert malingering when the available pulmonary function or other diagnostic tests can be readily faked by the perpetrator and afford little confidence in discerning genuine illness from fraud. Therefore, improved, inexpensive diagnostics that are less susceptible to fraudsters and that are able to provide such discernment, such as can be provided by some embodiments of the inventions are valuable and needed.

Prior attempts at pulmonary function testing methods that are brief and entail measurements over only one or a few breaths are highly susceptible to fraud. For example, it is relatively easy for the perpetrator to know and mimic forced-expiratory maneuvers that will yield FEV1 and/or FVC values associated with moderate to severe obstructive lung disease. In that regard, some embodiments of the present invention are a substantial improvement upon the prior art. Moreover thirty or more minutes' capnometry nonlinearity measurements, such as may be obtained for certain embodiments, are less likely to be deceived by malingerers. Specifically, it not plausible that a person could conceive and carry out a pattern of breathing that would generate an abnormal capnometry nonlinearity properties resembling those of genuine obstructive lung disease, nor is it plausible that a healthy person intent upon fraud could enact an abnormal pattern and maintain a complex series of respiratory maneuvers over the course of 400 or more breaths to successfully mimic obstructive respiratory impairment. Conversely, it is conceivable that an unhealthy person with actual obstructive lung disease might, with considerable and sustained effort aimed at mimicking a normal respiratory state, exhibit normal or near-normal capnometry nonlinearity score. However, even this possibility is decidedly unlikely during measurements lasting 30 minutes or more.

Some pulmonary medicine efforts have occasionally employed certain nonlinear analytics such as DFA; however, DFA in pulmonology has primarily addressed PEF, FEV1, and other non-capnometric measurements and has not been directed to determining the risk of acute respiratory distress or acute pulmonary function decompensation events requiring emergent attention by a physician.

Ventilation is influenced by gravity and body habitus, and therefore traditional capnometry is notably susceptible to artifacts having to do with transient changes in ventilation-perfusion matching. When the patient is upright (standing or seated), abdominal contents are pulled downward and the lower lobes of the lungs receive most of the blood flow while the upper lobes receive most of the ventilation. With supine or semi-reclining positions, the diaphragm excursion into the belly is less and ventilation and perfusion disparities between upper and lower lobes are reduced, resulting in smaller difference between venous pCO2 and etCO2.

Other sources of confounding of approaches to the problem include pulmonary compliance, psychological factors, and patient cooperation. Airway constriction in reaction to stressful or anxiety-provoking stimuli in asthma depends on an intact cholinergic pathway, is chiefly associated with the central airways, and largely eludes detection by conventional measures of airway physiology, including traditional spirometry, oximetry, and capnometry. Some embodiments of the present invention are able to detect emotionally-induced obstructive effects, largely owing to the nonlinear time series method and a substantially longer sampling interval compared to conventional exams.

Furthermore, it is widely known that persons being examined in a medical setting with capnometry during spontaneous breathing may breathe in such a way as to exhibit larger-than-normal tidal volumes, due to the patients' wish to conform to what they perceive to be the desire of the clinician who is examining them. While these patterns of altered breathing may be sustained by the patient for exams that only last a few tens of seconds, it is highly improbable that such patterns will be sustained for tens of minutes. Thus, some embodiments of the present invention tend to reflect the natural diversity of breathing patterns that prevail over observation periods that are 30 or more minutes in length. Such longer observation intervals afford the possibility to measure patterns that arise with lower frequency than are within the scope of traditional examination methods that only acquire data over short periods of a few seconds.

Conventional capnometry-based monitoring systems have been shown to have inadequate statistical sensitivity and specificity for the purpose of predicting respiratory events. When measurements rely upon spirometry or oximetry or conventional capnometry patterns as the trigger or sentinel event for predicting incipient pulmonary function decompensation, the predictions are generally only relevant when the person is already experiencing significant pulmonary function deterioration.

Additionally, many prior approaches involve cumbersome, complex, expensive and/or invasive instrumentation, or require a skilled operator in attendance. For example, the most accurate approaches, such as isotopically-labeled gas diffusion methods, are expensive, are not widely available, are only performable by subspecialty-trained providers, and are only applicable to a small subset of patients who are already known to be at high risk.

Other recently-introduced efforts involve expensive measurements, such as genomic or proteornic laboratory tests that are not widely available and that have a performance turnaround time of many hours or days before the results and prediction are available for use, such that the prediction or classification is not timely with respect to interventions aimed at preventing the predicted occurrences.

Additionally, some approaches are sensitive to, and may be compromised or entirely confounded by, individual variations in patient anatomy and activities, such as transfers from chairs or wheelchairs or beds, transfers with slide-boards or grab-bars other prosthetics, patient movement and positioning, diurnal variations, etc. Similarly, the methods of these approaches may be compromised or entirely confounded by, individual variations in operator positioning of the capnometer circuit on the patient or variations in the timing and method of acquiring the specimens or data that will enter into the prediction and classification.

Furthermore, one major deficiency of other approaches is false-negative error rate and the absence of immunity to differences in daily activities and behavior mix. Yet another deficiency is activity-specificity, for example, the ability to detect or predict pulmonary function decompensation while walking but not while climbing stairs or running.

Still a further deficiency arising from the fact that existing systems only take measurements during a very brief exam is that they do not take into account diurnal variations in persons' capabilities. By contrast, some face-mask circuit and mobile computing device-enabled embodiments of the present invention are wearable over periods of an hour or several hours and, thereby, achieve sensitivity to time-varying patterns in respiratory-risk.

Still further, no mathematical or biomechanical models have to-date appeared that are able to predict pulmonary function decompensation from a wheelchair or other prosthetic devices that are prevalent in rehabilitation or long-term care venues.

Moreover, none of the other approaches has examined mathematical nonlinearity properties of the measured capnometry time series, nor has the prior art made use of continuous realtime time series over short periods of many minutes for the purpose of determining likelihood of nearterm future exacerbations of pulmonary function abnormalities. Despite the existence of capnometer recording equipment for more than 20 years, the analysis of long-timeseries capnometry data is seldom performed and, even then, it is used only for management of hospital in-patients in intensive care units, titration of mechanical ventilator settings, and the like. Only small selected portions of the recorded timeseries data may be subjected to detailed analysis, and the rest are generally discarded unexamined or ignored. Accordingly, a system (including an apparatus) or method that is inexpensive, non-invasive, accurate in its characterization of pulmonary function decompensation risk based on timeseries acquired over several tens of minutes' time, and that accommodates a wide range of body morphologies and variations in breathing mechanics is needed and would be welcomed. In particular, such systems or methods, as provided by embodiments of the invention, would facilitate preventing important adverse outcomes, and better conserving care provider resources than typically would otherwise happen with respiratory events risk estimation by the methods of other approaches.

In light of the foregoing, improved predictive-preventive methods and systems are provided, and in some embodiments comprise prediction classification or decision-support alert signals emitted at logistically convenient times far enough in advance (such as hours or days, or weeks, in some embodiments) of a respiratory event's occurrence to allow for classification of risk and effective preventive intervention in a majority of cases. Moreover, these embodiments provide additional advantages over other approaches, including that they are less expensive; amenable to use in an outpatient physician office or clinic with limited space and staff resources, and suitable for a much larger population who are at only a moderate risk of respiratory events. Accordingly, such embodiments find use as a tool not only for surveillance and triaging the patients who present with respiratory complaints to hospitals and other acute-care venues but also for ambulatory, free-living individuals who have one or more risk-factors for respiratory events.

Regarding respiratory preventive interventions, effective interventions vary, and optimal selection and personalized tailoring of them can depend upon the patient's context, gender, age, medications, comorbid diagnoses, history of previous respiratory events, and other factors. In the case of a moderately symptomatic ambulatory person, effective preventive interventions may include consultation with the personal physician or nurse for adjustment of medications regimen or behavioral and activity recommendations, or presentation at a nearby outpatient department for diagnostic assessment and monitoring. In the case of a person with existing, known respiratory conditions, effective preventive interventions may include referral to a pulmonologist, consideration for adjustment of medication regimen, or other alternatives.

Certain embodiments are not so much intended for usage during an episode of acute respiratory failure or during the first episode of an obstructive lung condition that is not yet chronic. Additionally, despite appropriate and compliant-adherent use of treatments such as β2-adrenergic agonists, anticholinergics, and inhaled corticosteroids and cognitive-behavioral measures, break-through episodes of acute respiratory distress do still occur. Accordingly, some embodiments aim to predict and prevent a large percentage of these. Indeed, such episodes constitute one major focus of certain embodiments provided herein inasmuch as these embodiments are not primarily directed toward identifying and diagnosing persons with previously unrecognized and untreated obstructive lung disease, nor are they directed to the management issues of previously-diagnosed persons who have been prescribed a suitable, effective regimen but who do not adhere to it. Rather, these embodiments may provide utility primarily (a) for therapeutic decisions and medications titration in reasonably therapy-adherent persons with refractory obstructive lung conditions of some months' or years' standing, in whom a propensity for recurring episodes of decompensation is already manifest and (b) for evaluating possible non-adherence to a plausibly effective regimen.

In the large percentage of patients in whom upper respiratory tract infections (URTIs) are the primary trigger for acute pulmonary function decompensation, embodiments of the invention may help to guide preventive interventions for infection prophylaxis.

Some embodiments may also be of use in gate-keeping decisions regarding "step" therapy with agents such as immunotherapies (e.g., omalizumab) or phosphodiesterase-4 (PDE4) inhibitors (roflumilast) or bronchial thermoplasty, or in implementing intensified monitoring with pulmonary function testing or frequent exhaled nitric oxide monitoring or case-management services-interventions that are applied according to cost-effectiveness policies that select patients according to criteria that warrant the incremental expense.

Figure 2A:
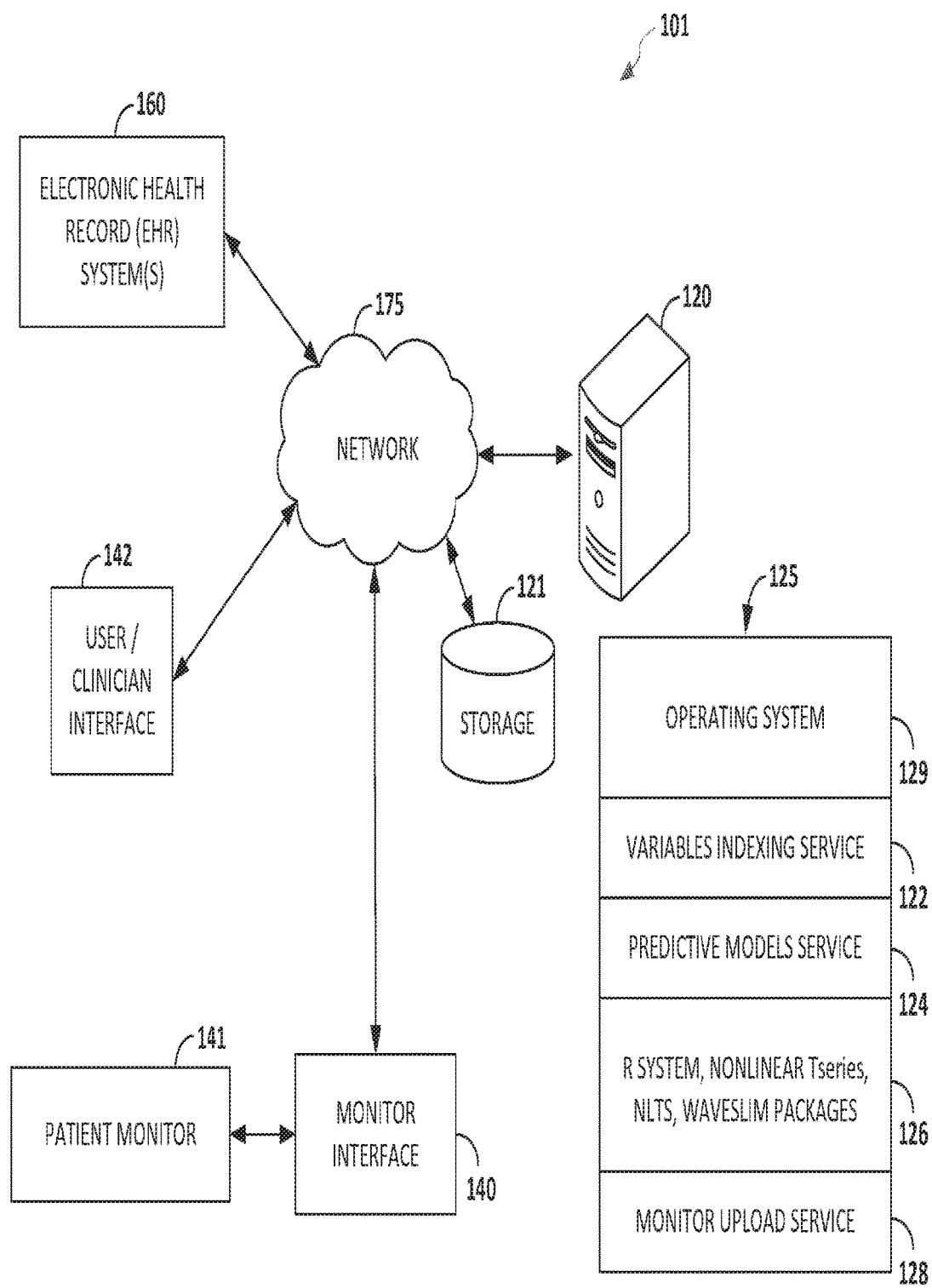
FIGS. 2A-2B depict aspects of an operating environment suitable for practicing an embodiment of the invention.
Figure 2B:
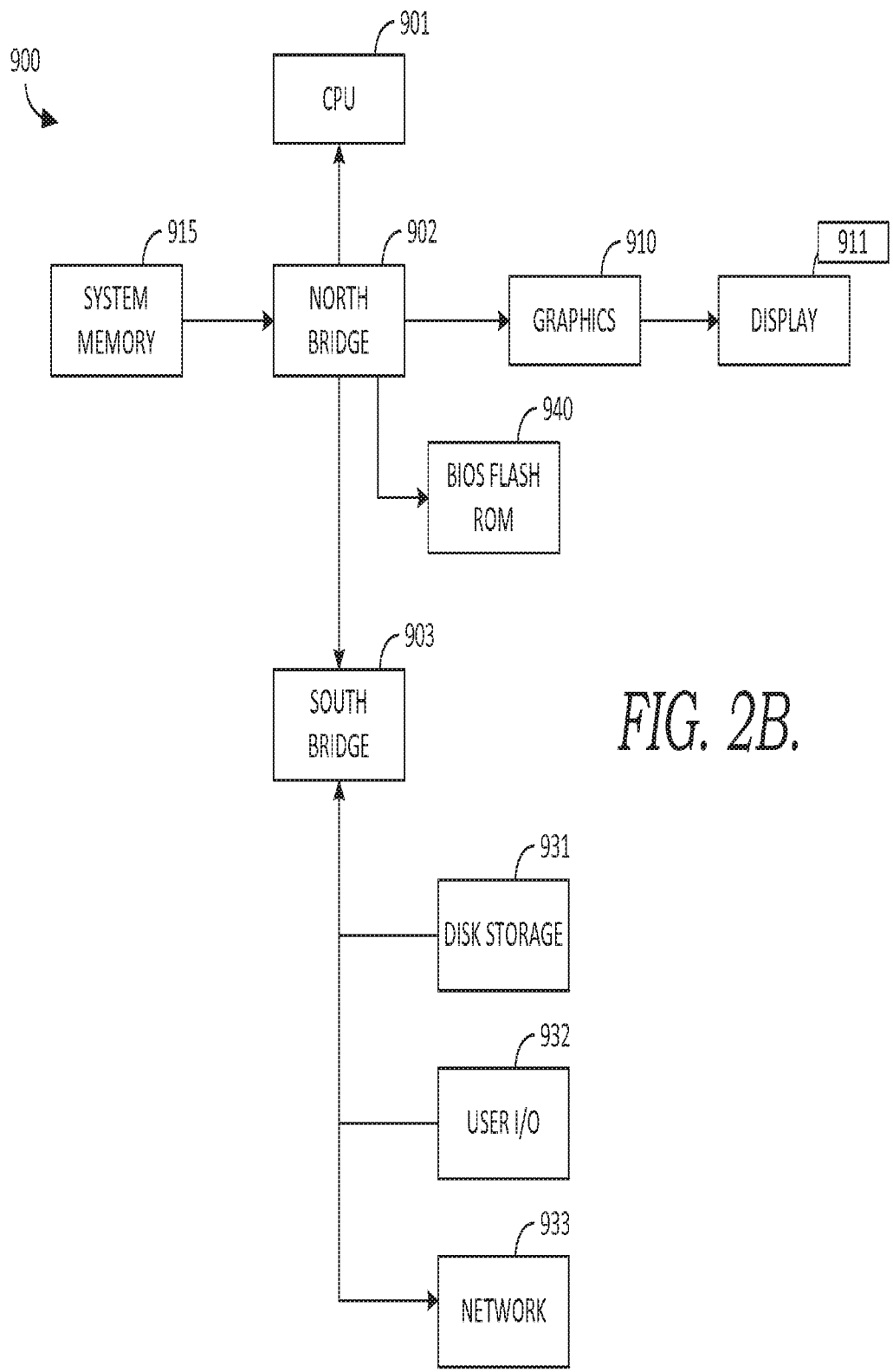

Turning now to FIGS. 1, 2A and 2B, exemplary operating environments for an embodiment the invention are described and relate generally to the description of a mobile wearable system suitable to be utilized for timeseries nonlinearity properties-based prediction and prevention of acute respiratory distress. Referring to the drawings in general, and initially to FIG. 1 in particular, an exemplary operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, environment 100 includes one or more sensors 116. In one embodiment, sensor(s) 116 include one or more transducers or types of sensors operable for providing electrical signals corresponding to measurements of various conditions or states of a user, as further described below. Embodiments of sensor(s) 116 may further include a power supply, processor, memory operable for acquiring and storing user-information and programming instructions, and communication component for communicating the resulting measurements of user-information with processing/communication component 130.

In some embodiments, sensor(s) 116 includes one or more capnometeric transducers operable to determine capnometer measurement of CO2 partial pressure and to provide signals corresponding to the time course of changing CO2 concentration in the stream of expired air. For example, in some embodiments, sensor(s) 116 includes one or more transducers, which can take the form of infrared phototransistor capnometer sensors, for obtaining electrical CO2 signals from the individual. In one embodiment, a non-dispersive infrared (NDIR) illumination source is utilized, consisting of either a broad-spectrum infrared source such as an incandescent lamp filament or glow-bar. NDIR embodiments employ a narrow-bandpass interference filter in the optical path, to restrict the incident light on the sensor to one of the bands in which CO2 exhibits significant absorption (e.g., 4.260 μm or 2.004 μm). In another embodiment, dispersive illumination from a narrow-spectrum infrared source such as an LED diode or a laser diode is used, with said source having peak emission at the desired band. The spectrometry may be either single-wavelength or dual-wavelength, and concentration of CO2 is determined from the optical absorbance measurements according to the widely-known Beer's Law.

In some embodiments, a processor for sensor(s) 116 (which may be embodied as component 130, described below, or as a separate processor for controlling one or more sensor(s) 116) is operable to control the frequency of measurements; for example, to read a transducer's output at certain intervals such as 10 or more times each second; to pre-process or condition the signal, including applying a threshold, noise-filter, or normalizing the raw user-derived signal; read from or store the user-information in memory, and communicate the acquired timeseries of user-information to component 130 via a communication component of sensor 116. In one embodiment, a floor-threshold is applied such that only measurements of a certain magnitude or within desired parameters are acquired and communicated to component 130. For example, it may be desirable in some embodiments not to capture every breath of the user, but rather only breaths that exhibit morphology denoting the patient's conformance to the sampling protocol.

In one embodiment, sensor(s) 116 include one or more capnometers, flow meters, or combination of such devices as to enable one or more sensor(s) 116 to detect user breathing, user position or orientation, and sudden changes in user position. In these embodiments the timeseries of user-information communicated to component 130 may comprise individual capnometry CO2 concentration values, with each new CO2 measurement adding a member to the timeseries. In other words, there could be irregular periods of time between capnometrys that are captured by sensor(s) 116.

In one embodiment, such a sensor 116 may be optimally positioned on the user. In such an embodiment, a computing device, which may be embodied as a mobile device, such as a smart phone, running a program for determining timeseries nonlinearity measures, may monitor user capnometry timeseries and provide to the user and health-care provider early earning warning of a likelihood of increased risk of acute respiratory distress. In one embodiment, sensor(s) 116 are embodied as one or more capnometric devices, such as the Massimo Emma®, produced by the Massimo Corporation of Irvine Calif., the CapONE TG-900 series, produced by Nihon-Kohden, Phillips Respironics NM3, or similar devices. Some of these devices also include functionality described in connection to processing/communication component 130, described below.

Continuing with FIG. 1A, environment 100 includes processing/communication component 130, which is communicatively coupled to sensor(s) 116, storage 192 and backend 190. Exemplary embodiments of component 130 include one or more processors operable for processing user-sensor information and determining copnometry measures and nonlinearity, a communication module for receiving information from one or more sensor(s) 116 and for communicating results to the user or health-care provider, and a memory (which may be embodied as storage 192) for storing received user-information, determined results, and programming instructions. In some embodiments, component 130 may worn on the user's body, such as clipped to a belt, in a holster, or around the user's waist, torso, or neck, or can be carried by the user, such as in the user's pocket or purse, or may be kept with a close enough proximity to the user as to communicate with sensor(s) 116. In some embodiments, sensor(s) 116 are housed within or on component 130, and in some embodiments, one or more features or subcomponents of sensor(s) 116 and component 130 may be integrated, thereby eliminating or reducing noise, interference, distortion, ambient atmospheric pressure, water vapor pressure, or artifacts and also improving ease-of-use and patient compliance.

Some embodiments of component 130 comprise a smart phone running one or more application programs or "apps" for receiving user-sensor information, determining capnometric-related measures or statistics, and storing and communicating results to the user and health care provider. In some smart-phone embodiments, component 130 uses the phone's communication equipment for communicating user information to a backend 190, such as a health care provider or decision-support knowledge agent. Component 130 may use other communication features of the smart phone such as Bluetooth or Wi-Fi to communicate with one or more sensors 116 and in some embodiments, a base station, user computer, or user/clinician interface, such as described in connection to FIG. 2A.

A smart phone may be communicatively-coupled with an additional component for facilitating communication with one or more sensors 116, for processing user-information, or for storing and communicating user results. For example, in one embodiment, component 130 is communicatively-coupled to a holster or other component containing a communication module for communicating with one or more sensor(s) 116. Such an embodiment is useful where sensor(s) 116 use a communication protocol that is not compatible with component 130. For example, where sensors communicate using Bluetooth, but component 130 is embodied on non-Bluetooth enabled smart phone, the user may attach a Bluetooth module to the smart phone to enable it to communicate with sensors 116. Similarly, where sensor(s) 116 communicate using Zigbee or another low-rate wireless personal area network platform, a user may couple a Zigbee-enabled communication module to their smart phone. In another example embodiment, a smart phone may be communicatively-coupled with a base station (not shown) located in the user's house. In one embodiment, the base station could be a personal computer connected to a wireless router or a laptop equipped with RF communication capability such as Wi-Fi or Bluetooth. In one embodiment, the base station communicates with backend 190.

In another embodiment, processing/communication component 130 communicates directly with backend 190. Backend 190 includes the health care provider computer system and devices, case-management software, electronic health record decision-support systems and devices, and consumer personal health record systems and devices. In some embodiments, brick 130 stores information on data store 192, which may be local or remotely located, and which may be accessible by backend 190, in some embodiments. In some embodiments, data store 192 comprises networked storage or distributed storage including storage on servers located in the cloud. Thus, it is contemplated that for some embodiments, the information stored in data store 192 is not stored in the same physical location. For example, in one embodiment, one part of data store 192 includes one or more USB thumb drives or similar portable data storage media. Additionally, information stored in data store 192 can be searched, queried, analyzed via backend 190, such as by a health care provider or by a decision-support knowledge agent, for example.

In some embodiments, sensor(s) 116 communicate with other sensors 116 and with component 130 over a wired or wireless communication protocol. In one embodiment, sensor(s) 116 communicate using Bluetooth, Wi-Fi, or Zigbee protocols. In some embodiments a low-powered communication protocol is desirable in order to preserve the batter life of the sensor(s) 116. In some embodiments using a communication protocol having a narrow bandwidth, such as Zigbee, sensor(s) 116 may also include a memory buffer for storing user-derived information until it is communicated to component 130. Sensors 116 may also communicate with other sensors 116 or directly with a base station, in some embodiments.

As described above, embodiments of processing/communication component 130 are communicatively coupled to one or more sensor(s) 116, such as a wearable capnometry sensor, which is one embodiment of sensor(s) 116. In some embodiments, component 130 and/or sensor(s) 116 are capable of being coupled to a docking station or base station (not shown), which recharges a battery or other power supply in component 130 and or sensor(s) 116.

Turning now to FIG. 2A, an aspect of an operating environment suitable for practicing an embodiment of the invention is shown and referenced generally as 101. Example operating environment 101 includes a computerized system for compiling and/or running an embodiment of an acute respiratory decompensation event prediction service, and may be used for generating an ensemble classifier and verifying and validating whether such a detector achieves statistical sensitivity and specificity in the intended mortality range of deployment, sufficient for satisfactory performance in the use for classifying patients according to in-hospital mortality outcome.

With reference to FIG. 1C, one or more electronic health record (EHR) systems, such as hospital EHR system 160 are communicatively coupled to network 175, which is communicatively coupled to computer system 120. In some embodiments, components of operating environment 101 that are shown as distinct components may be embodied as part of or within other components of environment 101. For example, EHR system(s) 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system(s) 160 may perform functions for two or more of the EHR systems (not shown) in FIG. 2A.

In embodiments, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 101 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health records, which may be stored on storage 121, and may further include one or more computers or servers that facilitate the storing and retrieval of the health records. In some embodiments, EHR system(s) 160 may be implemented as a cloud-based platform or may be distributed across multiple physical locations. EHR system(s) 160 may further include record systems, which store real-time or near real-time patient (or user) information, such as wearable, bedside, or in-home patient monitors 141, for example.

Although FIG. 1A depicts an EHR system(s) 160, it is contemplated that some embodiments may rely on monitor interface 140 and/or patient monitor 141 for storing and retrieving patient record information such as information acquired from patient monitor 141.

Example operating environment 101 further includes provider user/clinician interface component 142 communicatively coupled to network 175. Embodiments of interface 142 may take the form of a user-clinician interface operated by a software application or set of applications on a client computing device such as a personal computer, laptop, smartphone, or tablet computing device. In one embodiment, the application includes the PowerChart® software, manufactured by Cerner Corporation. In an embodiment, the application is a Web-based application or applet. A provider clinician application facilitates accessing and receiving information from a user or health care provider about a specific patient or set of patients for which a respiratory-event-risk assessment is to be performed and facilitates the display of results, recommendations or orders, for example. In some embodiments interface component 142 also facilitates receiving orders for the patient from the clinician/user, based on the results. In some embodiments, interface component 142 may also be used for providing diagnostic services.

Example operating environment 101 further includes computer system 120, which may take the form of a server, which is communicatively coupled through network 175 to EHR system(s) 160, storage 121, and monitor interface component 140.

Embodiments of user monitor interface component 140 may take the form of a user interface and application, which may be embodied as a software application operating on one or more mobile computing devices, tablets, smart-phones, front-end terminals in communication with back-end computing systems, laptops or other computing devices. In some embodiments, monitor interface component 140 includes a Web-based application or set of applications that is usable to manage user services provided by embodiments of the invention. For example, in some embodiments, monitor interface 140 facilitates processing, interpreting, accessing, storing, retrieving, and communicating information acquired from patient monitor component 141. In some embodiments, monitor interface 140 is used to display user (or patient) information relating to breathing and risk for acute respiratory decompensation event. In some embodiments of monitor interface 140, an interface component may be used to facilitate access by a user to functions of information on patient monitor 141, such as operational settings or parameters, user identification, user data stored on monitor 141, and diagnostic services or firmware updates for monitor component 141, for example.

As shown in example environment 101, monitor interface component 140 is communicatively coupled to patient monitor component 141 and to network 175. Embodiments of patient (or user) monitor component 141 may comprise one or more sensor(s) 116, described in connection to FIG. 1, and in some embodiments, monitor component 141 and interface component 140 comprise processing/communications component 130 and one or more sensor(s) 116, described in connection to FIG. 1.

Embodiments of monitor component 141 may store user-derived data locally or communicate data over network 175 to be stored remotely. In some embodiments, monitor interface component 140 is wirelessly communicatively coupled to monitor component 141. Monitor interface 140 may also be embodied as a software application or app operating on a user's mobile device, and in an embodiment may facilitate uploading of motion information from monitor 141 to computer system 120. In some embodiments, monitor interface 140 and monitor 141 are functional components of the same device, such as a device comprising a sensor and a user interface. In some embodiments, monitor interface 140 is embodied as a docking station or base station, which may also include functionality for charging monitor 141 or downloading information from monitor component 141. In some embodiments, monitor interface 141 is not part of the application on computer system 120 for interfacing with monitor 141 (sensor(s) 116), such as receiving motion information from monitor 141.

As previously described, in some embodiments patient monitor component 141 and monitor interface component 140 are embodied an sensor(s) 116 and processing/communication component 130. One embodiment comprises capnometric devices, such as Massimo Emma®, produced by the Massimo Corporation of Irvine Calif., the CapONE TG-900 series, produced by Nihon-Kohden, Phillips Respironics NM3, or similar devices, wherein interface component 140 comprises the user-interface functionality provided by these devices.

Continuing with FIG. 2, some embodiments of monitor component 141 and/or monitor interface component 140 include functionality for processing user-derived information locally or for communicating the information to computer system 120, where it is processed. In some embodiments, the processing may be carried out or facilitated by one or more software agents, as described below. In some embodiments the processing functionality, performed by processing/communication component 130, which may occur on monitor component 141, monitor interface 140, and/or computer system 120 includes signal conditioning, such as removing noise or erroneous information.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone. In one embodiment, computer system 120 comprises processing/communication component 130 and/or backend 190, described in FIG. 1, or aspects thereof.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 140 and/or interface 142 operates in conjunction with software stack 125.

In embodiments, variables indexing (or mapping) service 122 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke software services 126. In one embodiment software stack 125 includes predictive models service 124, which comprises the services or routines for determining nonlinearity measures of capnometry-information or respiratory-related-information timeseries and performing an ensemble of measures, such as example program 700 illustratively provided in FIGS. 7A-7C.

Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, nonlinear Tseries, nlts (nonlinear time series), and waveslim packages, or similar services. In some embodiments, software services 126 are associated with file system frameworks, such as non-distributive file systems or distributive file systems, such as provided the Apache Hadoop and Hbase framework, which in some embodiments facilitate provide access to cloud-based services such as those provided by Cerner Healthe Intent®.

Example operating environment 101 also includes storage 121 or data store 121, which in some embodiments includes patient data for a candidate or target patient (or information for multiple patients); variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160 and/or storage 192 of FIG. 1. Further, although depicted as a single storage data store, data store 121 may comprise one or more data stores, or may be in the cloud.

Turning briefly to FIG. 2B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 2B is provided as one example of any number of suitable computer architectures, such as computing architectures that support local, distributed, or cloud-based software platforms, and are suitable for supporting computing system 120.

Returning to FIG. 2A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 3A:
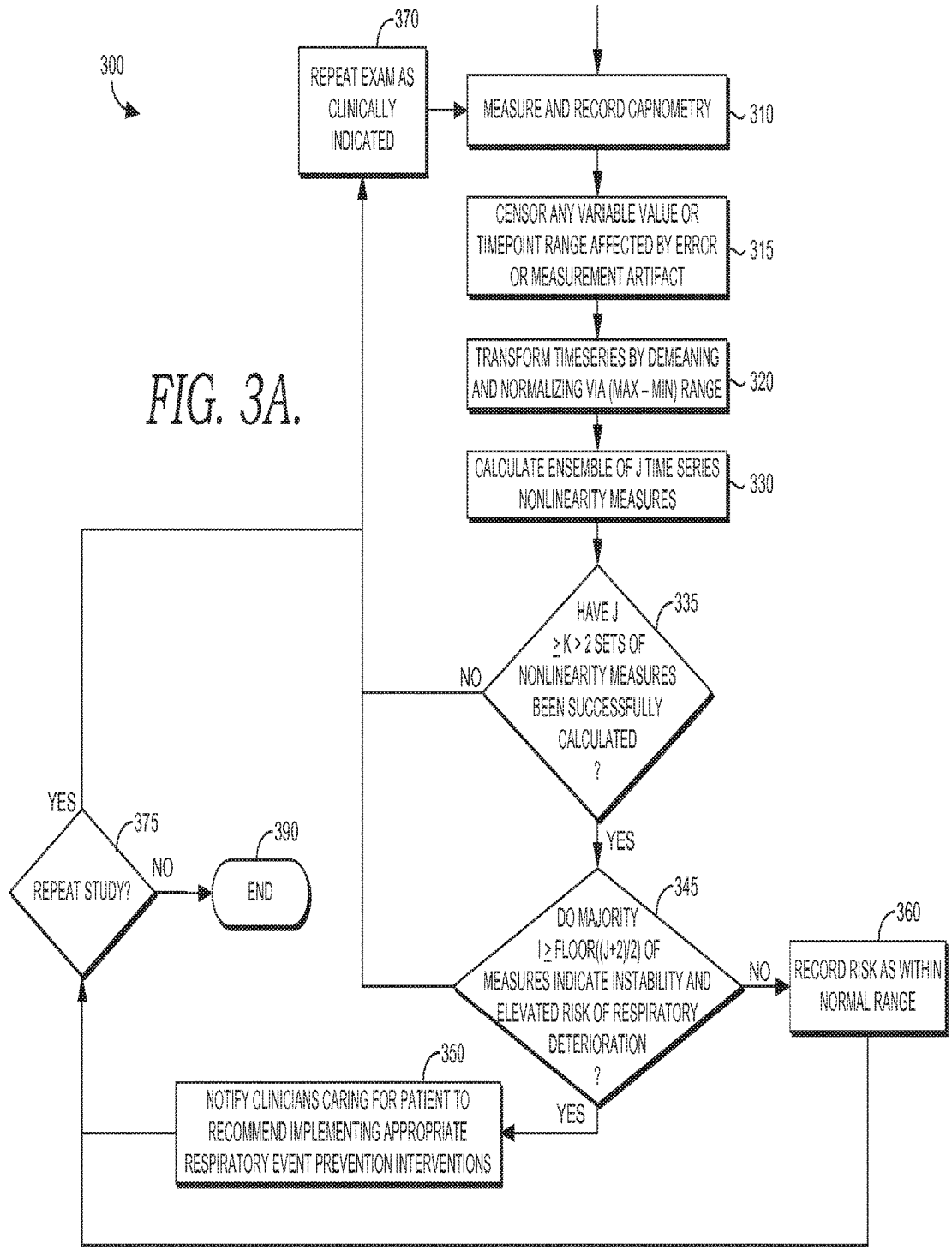
FIG. 3A depicts a flow diagram of a method for automatically predicting dyspnea and acute respiratory distress risk in an individual with an obstructive pulmonary condition, where the distress is of a type and severity as are likely to result in unplanned requirement for attention in a hospital or emergency department, in accordance with embodiments of the invention.

Turning now to FIG. 3A, a flow diagram is provided illustrating one exemplary method 300, in accordance with an embodiment of the invention. As described previously embodiments of the invention provide a computerized system, methods, and computer-readable media for automatically identifying persons who are at risk for pulmonary function decompensation through the use of a system, which in one embodiment, includes noninvasive, portable, wearable electronic device and sensors equipped with signal-processing software and statistical predictive algorithms that calculate timeseries nonlinearity measures, derived from a digital capnometric-signal timeseries acquired by the device. The measurements and predictive algorithms embedded within the device provide for unsupervised use in general acute-care and chronic-care venues and afford a degree of robustness against variations in individual anatomy and sensor placement.

Some embodiments are therefore able to provide a leading indicator of near-term future abnormalities, proactively alerting the clinicians caring for the person with sufficient advance notice to enable effective preventive maneuvers to be undertaken. In one exemplary embodiment, the device is integrated with case-management software and electronic health record decision-support system.

By way of example and not limitation, a user using one embodiment of the invention may be able to breathe into the capnometry sensor apparatus in an outpatient office or clinic for a short interval of time, such as 30 minutes for example, during which capnometry measurements are acquired for 400 or more breaths taken by the person, digitized at a sampling rate preferably at 10 Hz or greater at 12 bits precision or more. In one embodiment, the user may don one or more sensors capable of acquiring capnometer measurements, which could include a sensor affixed via a mouthpiece and check-valved breathing circuit or by similarly-equipped nasal prongs or a facemask that seals tightly about the subject's mouth and nose, and the acquired sensor data are temporarily stored in a memory unit in the sensor device itself (e.g. sensor(s) 116) and later communicated from the device to a processing system (e.g., computer system 120 and/or processing/communication component 130).

In one example embodiment, the computer system may include one or more software program services, which may be embodied as an application or app, which when executed receives user data from the sensor-device or storage 121, calculates a plurality timeseries nonlinearity measures, combines these in a mathematical ensemble model, and communicates the composite ensemble results to the clinician user, case-management software, decision-support systems, or electronic health record systems. For example, the system may notify the user in advance, via a notification message or electronic mail, and may also notify the user's health plan, electronic-health record decision-support systems or personal health record systems, via a call, HTTP, SMS text-message, or other form of electronic or radiofrequency communication, that the user has an increased likelihood of a near-term future abnormality or respiratory occurrence. This enables the care providers to take appropriate preventative measures.

With reference to FIG. 3A, at a high level, method 300 illustratively depicts a method for determining a capnometry nonlinearity score (CNS) for an individual. The CNS may be determined by applying an objective function to user-derived information such as capnometry-signal information obtained from the one or more sensors 116. Some embodiments of the invention process the information to calculate a CNS(t) timeseries, where t represents time, as a function of the individual's instantaneous CNS determinations.

Method 300 uses an ensemble model based on a poll or "vote", such as but not limited to a "majority vote", although this is shown, among a plurality of measures of capnometry time series nonlinearity as a continuous or discrete function of time is utilized, such as the Likelihood Ratio metric, White test, Terasvirta metric, McLeod-Li metric, Tukey 1-df metric, and time-reversibility metric are exemplary quantitative measures of the nonlinearity of timeseries. Relevant tests of the nonlinearity of timeseries as are known to those practiced in the art. In some embodiments, these may include: Likelihood Ratio test for threshold nonlinearity; White neural network test for nonlinearity; Terasvirta neural network test for nonlinearity; McLeod-Li test for autoregressive conditional heteroscedascity (ARCH); Third-order time-reversibility statistic; Tsay's test for quadratic nonlinearity; Hinich test; Subba Rao-Gabr test; and/or Keenan's one-degree test for nonlinearity.

Prior to the method 300, a patient monitor 141, is initialized and attached to a user-patient, in some embodiments. For example, the sensor may be configured for the patient including adjusting sensitivity based on the particular patient or location(s) or types of the sensor(s) 116 of monitor 141. In some embodiments, monitor 141 may be configured so as to provide information to an EHR 160 associated with the particular patient.

Following initialization of monitor 141, at a step 310, capnometry signals of a user, such as a patient, are obtained using one or more sensors 116. In one embodiment, user-information representative of the capnometry signals is communicated from one or more sensors 116 to communication/processing component 130 or storage 121, where it may be subsequently processed. In one embodiment, sensor 116 captures capnometry waveforms corresponding to the user's movement, thereby resulting in a timeseries of capnometry-signal intervals. In some embodiments, information from approximately 400 breaths or about 30 minutes of breathing is obtained to accumulate capnometric or respiratory information.

At step 315, the received capnometry information may be cleaned or censored, if necessary or desired. For example, it may be necessary or desirable to scrub, eliminate outliers of received capnometry information or delete certain samples.

In steps 320 through 345, the capnometry nonlinearity score (CNS) as a function of the continuous or discrete capnometric timeseries is calculated. De-meaning is applied to remove baseline offset from the resulting signal, in some embodiments. Normalizing the maximal value of differences to the absolute magnitude of the signal may also be performed, in some embodiments, before calculating and updating the CNS(t) timeseries. Instructions carried on a computer-readable storage medium (e.g., for calculating CNS(t)) can be implemented in a high level procedural or object oriented programming language to communicate with a computer system, in one embodiment, such as example program 700 provided in FIGS. 7A-7C. Alternatively in another embodiment, such instructions can be implemented in assembly or machine language. The language further can be compiled or interpreted language, in one embodiment.

It is further contemplated that in some embodiments, the CNS-related processing occurring in steps 320 through 345 occurs in realtime or near realtime, simultaneously, as electrical capnometric signal-information is collected in step 310, thereby allowing a skilled operator to monitor an individual's CNS during pharmacologic or exercise physiologic stress, if desired. More generally, in some embodiments, processing steps 320 through 345 are performed substantially simultaneously with the step 310 of collecting the capnometric signals in near real-time, so as to enable the ambulatory patient to continue their ad lib breathing until at least 30 minutes have elapsed or until data from at least 400 breaths have accumulated.

At step 320, the received capnometric signals, comprising capnometry-information timeseries, are prepared for the nonlinearity measures. In some embodiments this preparation includes pre-processing or signal conditioning. Step 320 may be performed by sensor 116, by processing/communication component 130, or a combination. In embodiments, thresholding, artifact censoring, normalizing, noise filtering, or other DSP filtering, or any combination of these, may be applied to the raw signal information.

In one embodiment, ascertainment of the boundaries denoting the beginning and ending of a respiratory cycle is performed by first-derivative zero-crossing calculations or by the method of finite differences. When a new expiratory phase commences, the first gas to be expelled from the respiratory tree into the capnometer is air that has remained in the larger airways and throat, where little or no gas exchange occurs ("anatomical dead volume"). The CO2 concentration in the anatomical dead volume is very nearly equal to the CO2 concentration in ambient room air (~380 to 2,000 ppm). As such, the capnometry waveform at the onset of expiration is near ambient, and the onset is identifiable via the zero-crossing or thresholding of the first time derivative of the CO2 signal.

At a step 330, the ensemble of j timeseries nonlinearity measures is determined. In step 330 of j nonlinearity measures is first determined, or attempted, and compared to a reference value where successfully completed. Then an ensemble, such as described above, is performed on the k nonlinearity measures to determine a CNS score for the patient.

In particular, in some embodiments of step 330, the CNS timeseries is determined, a plurality of timeseries nonlinearity metrics are calculated, and used to determine the patient's acute risk of respiratory distress. By way of example and not limitation, the methodology of the invention may be understood through the following steps. Let the metrics consist of (a) the Likelihood Ratio test [LRT], (b) the White test, (c) Terasvirta's test, (d) the McLeod-Li test, (e) Tukey's i-df test, and (f) a time-reversibility test, all applied to a series of segments of the data comprising "moving windows" at least 100 breaths in length. Calculate p-values of the tests and accept the Hi alternate-hypothesis of "abnormal, deficient nonlinearity" if a majority-vote asserting abnormality is achieved among the following: $LRT > 1*10^{-3}$, $White > 1*10^{-2}$, $Terasvirta > 1*10^{-2}$, $McLeod-Li < 1*10^{-4}$, $Tukey > 5*10^{-3}$, $time-reversibility > -1*10^{-3}$. Each nonlinearity metric for timeseries acquired from low-risk 'normal' walking subjects (ones who do not experience a capnometric pulmonary function decompensation event in the near-term) has a value within a characteristic normal range for human ambulation, and this normal range of mild nonlinearity is for each metric reasonably insensitive to variations in age, gender, body morphology and size, time of day, over-the-ground walking surface, walking surface grade, and other factors. Linear or Gaussian-distributed timeseries properties denote or confer an increased risk of pulmonary function decompensation, as do severely nonlinear timeseries properties. By contrast, mild nonlinearity within the characteristic range for each metric is rarely associated with near-term respiratory events. In an embodiment the timeseries length M may vary between 400 to 1,000 samples, with accuracy generally increasing as the size of M increases.

In some embodiments of step 330, when a plurality of these metrics transgress their respective normal ranges which denote mild nonlinearity of normal, stable $CO_2$ gas exchange, the near-term likelihood of acute respiratory distress is increased, regardless whether the causation of respiratory events arises due to obstructive abnormalities in the bronchi and bronchioles of the respiratory tree, in the deep lung parenchyma, or via secondary causes, such as dementia, or neuromuscular, skeletal deformity, or other reasons.

In another embodiment, the evidence-combining method entails arithmetic averaging or median or other means of deriving a composite measure from the plurality of individual metrics in such a manner as to accurately reflect the predominant tendency or risk level. In another embodiment, the evidence-combining method entails a weighted linear sum reflecting the possibly non-uniform predictive evidentiary strength that is associated with the individual metrics, such as may arise due to varying sensitivity and/or specificity of the metrics, which may depend on the length of the timeseries, the number of steps encompassed by the timeseries, or factors pertaining to the power and efficiency of the metric's ascertainment of nonlinearity of the timeseries.

An example embodiment of computer instructions for carrying out step 330 (and other steps of the method 300) is illustratively provided in FIGS. 7A-7C as program 700. In this example, for each of the nonlinearity measures, rather than take the average or some other central tendency, the median is determined for each measure, and then compared to a reference value characteristic for normal human capnometry based on other parameters associated with the user, the venue (in some instances certain locations have elevated CO2 levels, such as may be produced by certain types of heating), or other factors.

At a step 335, in some embodiments a determination is performed as to whether enough nonlinearity measures have been obtained so as to perform the ensemble operation. In some situations, where j nonlinearity measures are undertaken, only k of them may compute or otherwise be sensitive of specific enough as to be used; some of them (j-k of them) may not converge, may be too insensitive/non-specific, or may otherwise yields unusable results. Thus for example, where 6 (j) nonlinearity measures are performed, only 3 (k) may yield a usable result. Accordingly, in this embodiment, at step 335 a determination is made as to whether enough nonlinear measures are available ($j \geq k > 2$; thus k=3 is sufficient). Where this condition is not satisfied, another nonlinearity measure may be undertaken. In some embodiments, the method proceeds to step 310, and capnometry information is received again. In some embodiments, the method proceeds instead back to step 330 (not shown) and one or more additional nonlinearity measures is performed on the already received motion information.

At a step 345, the "voting" or polling of the nonlinearity measures is performed to determine—in an embodiment—whether a majority of the nonlinearity measures indicate an elevated risk for a respiratory decompensation event. In some embodiments, only more than half of the nonlinearity measures need indicate instability, while in other embodiments, only one or another minimum number need indicate instability, wherein the minimum number is based on the particular nonlinearity measure, the patient, and clinician/caregiver preferences. In some embodiments, each nonlinearity measure gets one vote, and the votes are totaled, while in some embodiments, the measures are combined based on weights, which are determined based on past performance or clinician/caregiver settings. In an embodiment, a CNS or the determined risk for an acute respiratory decompensation event, determined at steps 330-345, is determined based on a ratio of the results of the nonlinearity models that were successfully calculated. For example, where each nonlinearity model (or measure) gets one vote and the votes are totaled, then where greater than 50% of the models indicate an abnormal result, then the patient is determined to have an elevated risk of respiratory distress.

In some embodiments, of step 345 it is determined whether the user's capnometry timeseries is showing signs of abnormal nonlinearity, based on the results of step 330. In one embodiment, if the stability is present, then the process returns to step 310 and additional capnometry timeseries information is obtained from monitor 141 (or from sensors 116).

If at step 345, the results of step 330 indicate the presence of abnormal pulmonary function decompensation-risk related nonlinearity, then the method proceeds to step 350.

At a step 350, a user, health care provider, or decision support system is notified that the user has an elevated acute risk of respiratory distress. In one embodiment, this instability indicates a change in the patient's condition, which may be for the better or worse. In one embodiment, a visual or graphical display of the electrical signals or a numerical or digitized representation of the monitored capnometry variables and CNS indices may be presented on a user's computer communicatively coupled to component 130, or a health care provider's computer communicatively coupled to backend 190. In one embodiment, a radiofrequency message may be emitted to security-/confidentiality-controlled, mated transceivers such as BlueTooth smartphones, Wi-Fi connections with personal computers or electronic medical records systems, and similar devices.

On the other hand, if at step 345, the results of step 330 do not indicate the presence of abnormal respiratory-distress-risk related nonlinearity, then the method proceeds to step 360, and the determined risk is recoded as within normal range.

At a step 375, in some embodiments, it is determined whether the patient is to be retested. Where the patient is not retested, the method proceeds to step 390; and where the patient is retested, the method may proceed ultimately back to step 310, through step 370, where the timeseries of capnometry is obtained again. In some embodiments, step 370 may specify parameters for repeating the method 300, such as the duration of time (or number of breaths) for obtaining the capnometry signal information.

Figure 3B:
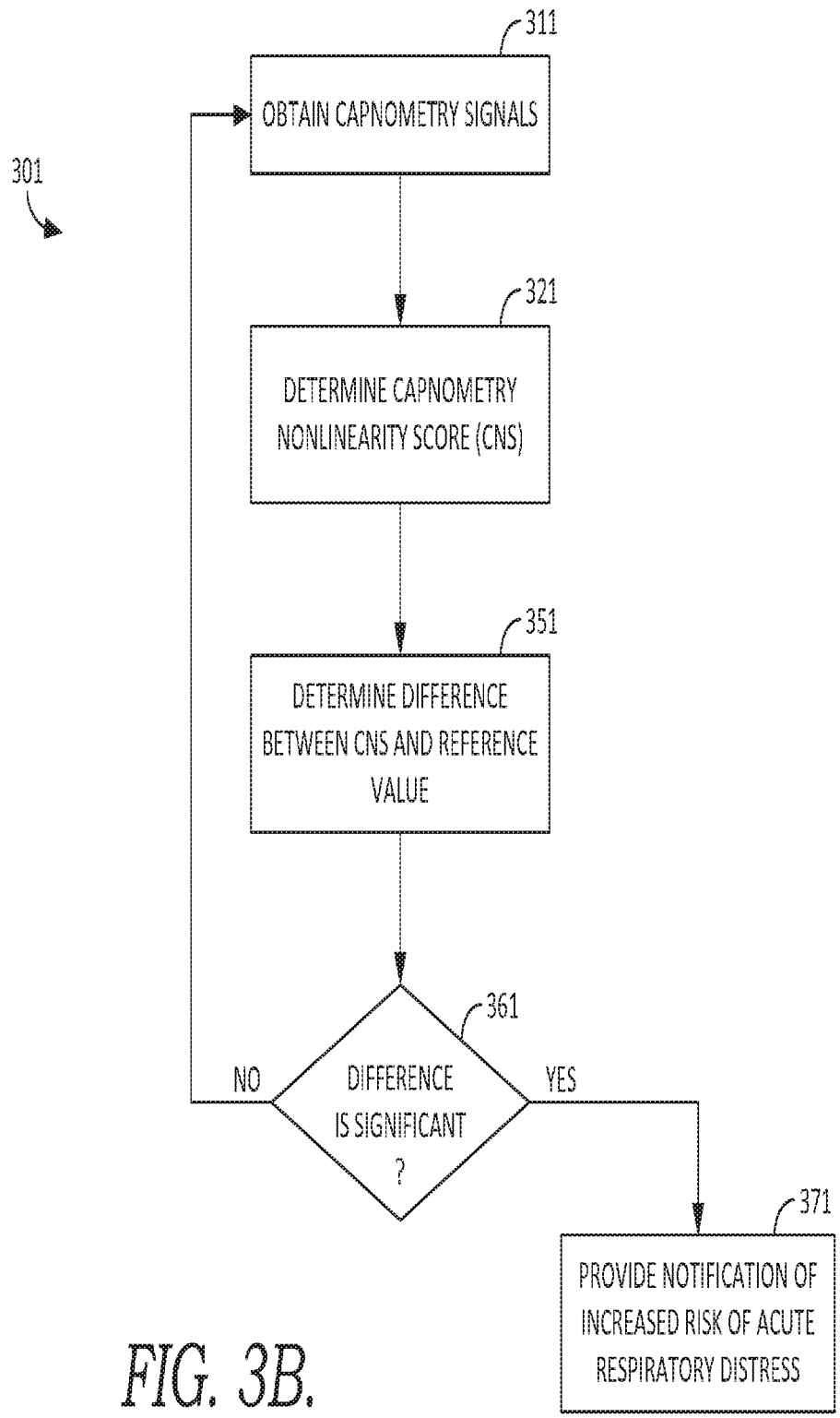
FIG. 3B depicts a flow diagram of a method for automatically predicting elevated risk of respiratory distress, in accordance with an embodiment of the invention.

Turning to FIG. 3B a flow diagram is provided illustrating an exemplary method for automatically predicting elevated risk of respiratory distress, according to one embodiment, generally referred to herein as method 301. At a high level, method 301 illustratively depicts a method for determining a capnometry nonlinearity score (CNS) for an individual. The CNS is determined by applying an objective function to user-derived information such as capnometric signal information obtained from one or more sensors 116. The method also includes determining the difference between the stability score value and a reference value to detect presence of instability of capnometry dispersion or other measurements.

It has been determined, as further described below in connection to that a significant difference between the two values indicates an increased risk of pulmonary function decompensation for an individual. In one embodiment, the reference value is selected based on other parameters associated with the user.

At a step 311, capnometry signals of a user are obtained using one or more sensors 116. User-information representative of the capnometry signals is communicated from one or more sensors 116 to processing/communication component 130. In some embodiments, pre-processing and conditioning of the capnometry signal information, which may include, for example, thresholding or flooring, artifact censoring, normalization, or DSP filtering, and other pre-processing and conditioning as described in connection with steps 315 and 320 in FIG. 3A, takes place either at the sensor 116, component 130, or both. At a step 321, CNS is determined in accordance with the method described in connection to steps 320 to 345 of FIG. 3A. At a step 351, the difference between the CNS and a reference value is determined. In one embodiment, the reference value is selected based one or more parameters associated with the user (or patient), the respiratory condition, testing environment, or preferences of the caregiver. In one embodiment, the reference value is set by the health care provider. Based on the results of this difference, at a step 361, a determination is made as to whether the difference is significant. In one embodiment, the difference is significant if the CNS exceeds the reference value. If the difference is not significant, then method 301 may terminate or may return to step 311 and wait to obtain additional signal information. On the other hand, if the difference is significant, then at a step 371, a notification may be provided such as described in connection to step 350 of method 300, in FIG. 3A.

Figure 4:
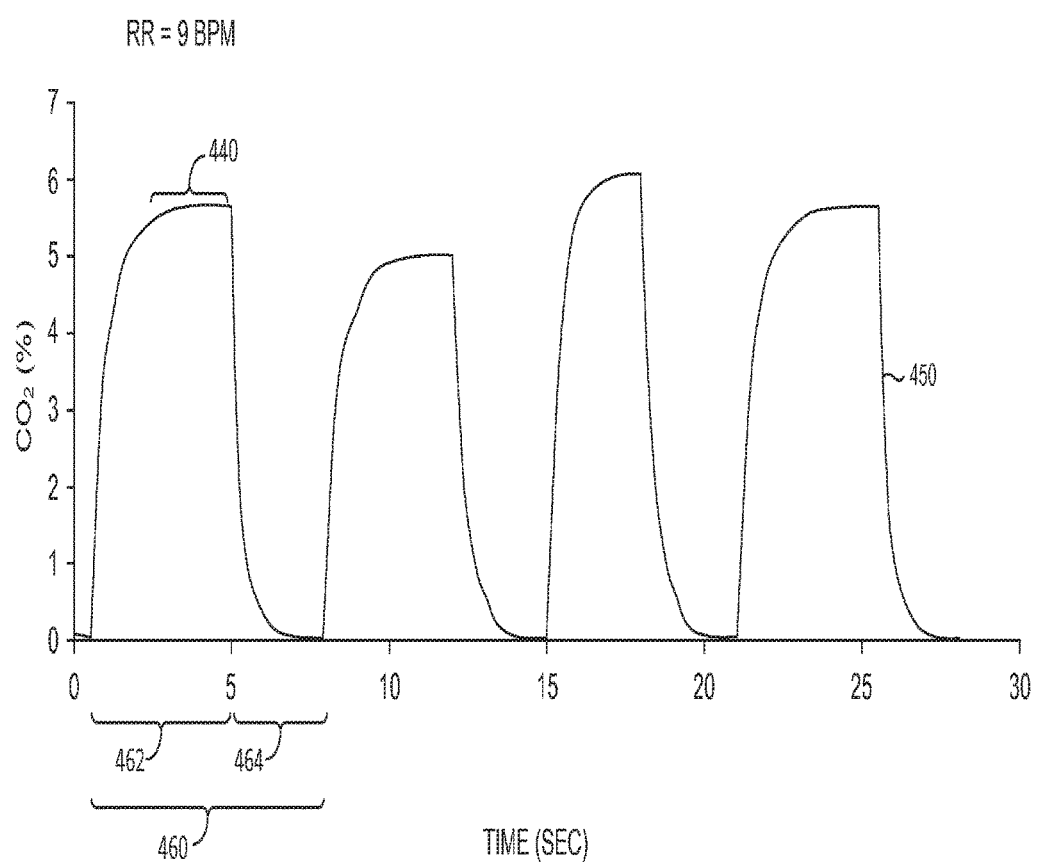
FIG. 4 depicts a portion of waveform representing a mixed-expiratory mainstream-sampled $feCO_2$ timeseries.

Turning now to FIG. 4, a portion of an example waveform representing a mixed-expiratory mainstream-sampled $feCO_2$ timeseries is provided and referred to generally as capnography curve 450. Curve 450 includes a series of respiratory cycles 460, each comprising an expiration portion 462 and inhalation portion 464. Each cycle 460 includes an end-tidal plateau phase 440. Curve 450 illustratively represents digitized measurements of an analog fractional expired carbon dioxide ($feCO_2$) signal, such a may be provided by sensor(s) 116, which in this instance are digitized at 100 Hz sampling rate using a commercially-available 12-bit analog-to-digital conversion module. In some embodiments, 400 end-tidal plateau phase 440 values are used for the caonometry timeseries. In one embodiment the last three values before a first derivative zero crossing are excluded.

By way of example, one embodiment of the invention, such as described in connection to FIGS. 1 through 3B and 7A-7C was applied using five positive experimental subjects between the ages of 11 and 60 suffering from moderate to severe bronchial asthma and/or emphysema based on usual clinical criteria, and having evidence of bronchial hyperresponsiveness. Each of the subjects had experienced no signs of bronchial infection for more than 30 days and continued their usual treatments (bronchodilator±inhaled corticoids±anticholinergics). Measurements were performed not less than 4 h after the last administration of short-acting β2-agonist inhaler. Eleven healthy control subjects between the ages of 9 and 54 with no known risk factors for pulmonary function decompensation were consented and studied. There were 5 acute respiratory distress events in the experimental cohort resulting in unplanned presentation to a hospital emergency department, as shown in table 610 of FIG. 6A. The control subjects were free of known disease except for hyperlipidemia and mild hypertension.

The capnographic measurements were performed with a specially-constructed mainstream-sampling circuit with an NDIR capnometer (e.g., patient monitor 141) operating at 4.260 μm (response time 250 ms; weekly calibration with a reference gas mixture (5% CO2)). The mouthpiece was inserted into the subject's mouth, with a soft elastomeric component to engage with the subject's upper and lower teeth. The lips were coapted to close around the mouthpiece and form a comfortable yet air-tight seal. Each subject breathed normally at a rate between 8 and 20 bpm throughout the conduct of the capnometry exam, inhaling air through the nose and exhaling through the check-valved capnometry circuit. The subjects watched videos or performed browsing or email on a laptop computer during a 30-min interval for the capnometry timeseries acquisition. The analog measurements of fractional expired carbon dioxide (feCO2) signal were digitized at 100 Hz sampling rate using a commercially-available 12-bit analog-to-digital conversion module. End-tidal carbon dioxide (etCO2) concentration was ascertained by determining end-tidal plateau (E3) phase by zero-crossing first-derivative calculations from the capnometry time series.

From a methodological point of view, due to physiological irregularities of respiration, in some embodiments, it is desirable to select good quality cycles according to criteria of duration, amplitude and, when possible, regularity of the capnography curve. For example, in one embodiment, respiratory cycles which do not meet the following criteria are censored out: 1) expiration lasting between 0.8 and 3.0 sec; 2) maximal CO2 concentration above 3.5%; and 3) good breath-to-breath regularity of rapid-rise phase (E2) and end-tidal plateau phase (E3). Additionally, in some outpatient office environments with forced-air heating, the cycling of the furnace may produce minute-to-minute fluctuations of 500 ppm (0.05%; 0.38 mmHg) CO2 or more in exam rooms with high air flux. In such cases, the use of the invention may require placement in an area that is well-stirred but not subject to such high air flux or is heated by hot water or electric rather than force-air means.

FIGS. 5B and 5A show a portion of the raw data (FIG. 5B) and curves 510 and 520 of FIG. 5A, depicting (with reference to the columns of FIG. 5B) raw_t vs. CO2 and raw_t vs. graph, respectively. (Example program 700 describes specific operations carried out on the sampled capnometry signal to determine the column values of FIG. 5B.)

Figure 6A:
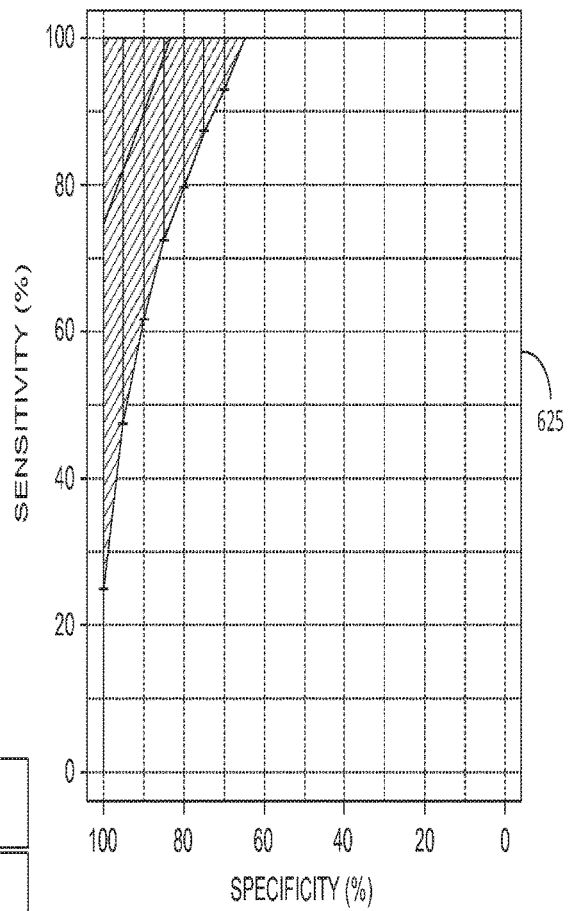
FIG. 6A depicts a Receiver Operating Characteristic (ROC) curve representing the accuracy and discriminating classificatory capacity of the invention in a cohort of 16 subjects, and tables showing the statistical performance of one embodiment of the invention in the initial cohort studied.

Continuing with the example embodiment, with reference to FIG. 6A, the determined CNS accurately predicted pulmonary function decompensation as shown in items 625 and 650 of FIG. 6A, where P<0.003 Fisher Exact Test, two-tailed. In the study connected with this example embodiment, the sensitivity of the CNS metric to predict pulmonary function decompensation was 80% and the specificity was 100%. The lower 95% confidence limit of the odds-ratio was >2.5 and the number-needed-to-treat (NNT) was 2. Item 625 of FIG. 6A shows the ROC curve representing the accuracy and discriminating classificatory capacity of this example embodiment on the cohort of 16 subjects. (FIG. 6B depicts one example of a computer program for determining this ROC curve.)

Insofar as a only small sample size of cases and controls was available, risk stratification by pulmonary diagnosis or other patient-grouping variables was not evaluated In this specific example. However it is contemplated that other embodiments may include specific submodels to predict pulmonary function decompensation in the presence of those covariables.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Accordingly, in one aspect, an embodiment of the invention is directed to a method for automatically predicting acute respiratory decompensation events that are likely to result in the need for acute medical attention in humans. The method includes obtaining capnometry signals representative of capnometry of an individual; detecting the presence of abnormal timeseries nonlinearity properties of capnometry measurements in said signals; determining, utilizing an objective function, a capnometry nonlinearity score (CNS) from said signals based on one or a plurality of previous time intervals; and determining a difference between a plurality of metrics comprising score and a reference value to classify the likelihood of events leading to pulmonary function decompensation within a future time interval, wherein a significant difference is indicative of an increased risk for acute respiratory distress. In some embodiments of the method, the objective function evaluates digitized capnometric capnometry timeseries from the one or a plurality of previous time intervals to classify the likelihood of a cascade of events leading to acute respiratory distress within a future time interval.

In some embodiments of the method, the objective function comprises a plurality of timeseries nonlinearity metric calculated from serially-acquired acceleration values acquired at a rate of not less than 10 samples per second for a duration not less than 30 minutes. Further, in some of these embodiments of the method, the results of the objective function are used by a decision-support algorithm to determine a quantitative risk for pulmonary function decompensation. Still further, in some of these embodiments, the decision-support algorithm is an ensemble model that combines nonlinearity measures for respiratory events-risk comprising at least 3 different timeseries nonlinearity measures.

In some embodiments of the method, the reference value is determined based on parameters associated with the individual including at least one of age, mobility, and pulmonary function decompensation history; wherein the determined difference is determined as significant when the difference exceeds a threshold; and wherein the threshold is based on a value indicative of minor fluctuations in activity level of the individual.

In some embodiments of the method, obtaining capnometry signals involves non-dispersive infrared spectrometry or dispersive infrared spectrometry in at least one optical band, and wherein the $CO_2$ gas possesses a strong absorptive band, such as bands at infrared wavelengths of 4.260 μm or 2.004 μm. Further, in some of these embodiments, the sampling method may be either via a mainstream circuit or sidestream-sampled capnometry circuit; the measurement means involves digitization of $CO_2$ in the range 300 ppm to 100,000 ppm, with at least a 12-bit digital precision and accuracy; the measurement means involves frequent sampling of the $feCO_2$ signal at a sampling rate of at least 10 Hz; the measurement means involves a sensor possessing response time constant of 500 msec or less; and/or the measurement means involves a breathing circuit having a contained volume ("mechanical dead volume") that is less than the "anatomical dead volume" of large airways (bronchi, trachea, mouth) of the human subjects whose respiratory function is to be determined.

In another aspect, an embodiment of the invention is directed to one or more computer-readable media having computer-executable instructions embodied thereon that when executed, facilitate a method for determining a capnometry nonlinearity score for an individual. The method includes, identifying capnometry information representative of expired carbon dioxide from an individual; and determining a capnometry nonlinearity score based on the capnometry information from one or a plurality of previous time intervals, for determining a likelihood of pulmonary function decompensation within a future time interval.

In yet another aspect, an embodiment of the invention is directed to a method for automatically predicting acute pulmonary function decompensation in humans. The method includes obtaining capnometry signals representative of capnometry of an individual; determining, utilizing an objective function, a capnometry nonlinearity score (CNS) from said signals based on one or a plurality of previous time intervals, to classify a likelihood of events leading to pulmonary function decompensation within a future time interval; and determining a difference between the score and a reference value, wherein a significant difference is indicative of an increased risk for pulmonary function decompensation.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for automatically predicting acute pulmonary function decompensation in humans the method comprising:
   obtaining capnometry signals representative of capnometry for an individual;
   generating a timeseries from the obtained capnometry signals;
   determining, via an objective function, a capnometry nonlinearity score (CNS) from the generated timeseries to quantify a likelihood of events leading to pulmonary function decompensation within a future time interval;
   determining a difference between the CNS and a reference value, wherein the difference exceeding a threshold is indicative of an increased risk for pulmonary function decompensation; and
   based on the determined difference exceeding a threshold, emitting an audible or visual notification.

2. The method of claim 1, further comprising:
   digitizing the obtained capnometry signals; and
   wherein the objective function evaluates the digitized capnometric timeseries to classify the likelihood of a cascade of events leading to pulmonary function decompensation within a future time interval.

3. The method of claim 1, wherein the generated timeseries is input in the objective function and comprises serially-acquired acceleration data.

4. The method of claim 1, wherein the results of the objective function are input in a decision-support algorithm that outputs a quantitative risk for pulmonary function decompensation.

5. The method of claim 4, wherein the decision-support algorithm comprises an ensemble model predictive algorithm that combines evidence from the results of a plurality of tests to establish a preponderant tendency or overall risk level.

6. The method of claim 1, wherein the method further comprises providing a notification to a health care provider when said increased risk for pulmonary function decompensation is indicated.

7. The method of claim 1, wherein the reference value is determined based on parameters associated with the individual including at least one of age, mobility, and pulmonary function decompensation history; wherein the determined difference is determined as significant when the difference exceeds a threshold; and wherein the threshold is based on a value indicative of minor fluctuations in activity level of the individual.

8. The method of claim 1, further comprising:
   communicatively coupling a capnometry sensor associated with the individual with an application executed by mobile device.

9. The method of claim 8, wherein the capnometry sensor has a sampling rate of at least 10 Hz.

10. The method of claim 1, wherein the objective function determines a normalized maximal value of differences of the signals included in the timeseries.

11. The method of claim 1, wherein the capnometry signals are generated at a rate of 10 Hz.

12. A system of for forecasting respiratory distress of an individual based on nonlinearity of capnometry signals, the system comprising:
    a remote capnometry sensor;
    one or more processors;
    computer-executable instructions that when executed by the one or more processors cause the processors to perform operations comprising:
    communicatively coupling with the remote capnometry sensor;
    obtaining capnometry signals representative of capnometry for an individual;
    generating a timeseries from the obtained capnometry signals;
    determining a capnometry nonlinearity score (CNS) from the generated timeseries to quantify a likelihood of events leading to pulmonary function decompensation within a future time interval;
    determining a difference between the CNS and a reference value, wherein the difference exceeding a threshold is indicative of an increased risk for pulmonary function decompensation; and
    based on the determined difference exceeding a threshold, emitting an audio or visual notification.

13. The system of claim 12, wherein the capnometry sensor has a sampling rate of at least 10 Hz.

14. The system of claim 12, wherein determining the CNS comprises normalizing a maximal value of differences of the timeseries via an objective function.

* * * * *

UNITED STATES PATENT AND TRADEMARK OFFICE
CERTIFICATE OF CORRECTION

PATENT NO. : 10,410,750 B1  
APPLICATION NO. : 15/855043  
DATED : September 10, 2019  
INVENTOR(S) : Douglas S. McNair Page 1 of 1

It is certified that error appears in the above-identified patent and that said Letters Patent is hereby corrected as shown below:

In the Specification

Column 11, Line 24: Please remove "Phillips" and replace with --Philips--.

Column 11, Line 28: Please remove "FIG. 1A" and replace with --FIG. 1--.

Column 12, Line 63: Please remove "and or" and replace with --and/or--.

Column 13, Line 9: Please remove "FIG. 1C" and replace with --FIG. 2A--.

Column 13, Line 55: Please remove "FIG. 1A" and replace with --FIG. 1--.

Column 15, Line 7: Please remove "Phillips" and replace with --Philips--.

Column 18, Line 23: Please remove "heteroscedascity" and replace with --heteroscedasticity--.

Column 19, Line 52: Please remove "i-df" and replace with --1-df--.

Column 19, Line 55: Please remove "Hi" and replace with --H1--.

Column 22, Line 43: Please remove "such a may" and replace with --such as may--.

Column 23, Line 66: Please remove "evaluated In" and replace with --evaluated in--.

In the Claims

Column 26, Line 34: Please remove "system of for" and replace with --system for--.

Signed and Sealed this  
Third Day of December, 2019

Andrei Iancu  
*Director of the United States Patent and Trademark Office*